United States Patent [19]

Morrison

[11] Patent Number: 4,526,982

[45] Date of Patent: Jul. 2, 1985

[54] 2,4-DIHYDRO-5-[(SUBSTITUTED)PHENYL]-4,4-DISUBSTITUTED-3H-PYRAZOL-3-ONES

[76] Inventor: Glenn C. Morrison, 1445 Arlington, Ann Arbor, Mich.

[21] Appl. No.: 497,316

[22] Filed: May 23, 1983

[51] Int. Cl.$^3$ ............................................ C07D 403/10
[52] U.S. Cl. ...................................... 548/336; 546/19; 546/211; 544/371; 548/302; 548/327; 548/214; 548/262
[58] Field of Search ......................................... 548/336

[56] References Cited

U.S. PATENT DOCUMENTS 4,377,697  3/1983  Fellner et al. ........................ 548/336

Primary Examiner—Robert T. Bond

[57] ABSTRACT 2,4-Dihydro-5-[(substituted)phenyl]-4,4-disubstituted-3H-pyrazol-3-one compounds as cardiotonic and antihypertensive agents, pharmaceutical compositions and methods of treating diseases with such agents as well as a process for the preparation of said compounds are described.

3 Claims, No Drawings

2,4-DIHYDRO-5-[(SUBSTITUTED)PHENYL]-4,4-DISUBSTITUTED-3H-PYRAZOL-3-ONES

BACKGROUND OF THE INVENTION 2,4-Dihydro-5-phenyl-4,4-dimethyl-3H-pyrazol-3-one is described in Bull. Soc. Chim. Fr., 1969, 4159 with no significant pharmacological activity prescribed.

SUMMARY OF THE INVENTION

The present invention relates to novel 2,4-dihydro-5-[(substituted)phenyl]-4,4-disubstituted-3H-pyrazol-3-one compounds useful as cardiotonic and antihypertensive agents having the structural formula (I):

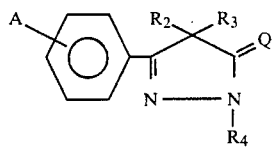

wherein Q is oxygen or sulfur; $R_2$ is lower alkyl; $R_3$ is lower alkyl or cyano, $S(O)_{0-2}R_2$, $OR_2$ or trifluoromethyl; $R_2$ and $R_3$ taken together can combine to form a three to six membered ring; $R_4$ is hydrogen or lower alkyl, and A is any of the groups from a to e, and is attached to the 3- or 4-position of the phenyl ring:

a.

A = 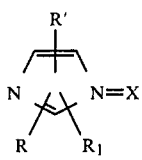

wherein $R_1$, R', and R are independently hydrogen or lower alkyl, $CH_2OH$, $SCH_3$, $SOCH_3$, $SO_2CH_3$, hydroxyalkyl, halogen, $(CH_2)_k NR''$, R''', wherein k is zero to two and R'' and R''' are independently hydrogen or lower alkyl, wherein lower alkyl contains one to six carbon atoms; or, when attached to the 4- and 5-positions of the imidazole ring, may be taken together to form a (i) 5-, 6-, or 7-membered ring which may also contain a nitrogen atom, (ii) benzene ring which is optionally substituted by halogen, hydroxy, lower alkyl, and lower alkyloxy, and (iii) pyridine ring; X is a bond, $(CH_2)_n$ or $O(CH_2)_{n+1}$ wherein n is one to four;

b.

A = 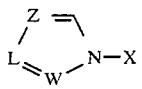

wherein
(i) W=L=Z=CH
(ii) W=Z=N and L=CH or
(iii) L=Z=N and W=CH, and X is the same as defined in 1a;

c.

A = (i) 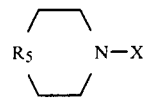

where $R_5$ is $CH_2$, O, S, $NR_6$ wherein $R_6$ is hydrogen, alkyl, $COR_7$ where $R_7$ is a benzene ring optionally substituted by halogen, lower alkyl, hydroxy, lower alkoxy, and $CF_3$ or $(CH_2)_n R_7$ where n is zero to four and $R_7$ is the same as defined above; or (ii) 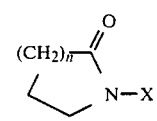

wherein n is one to three; or (iii) 

wherein $R_8$ and $R_9$ are independently hydrogen, lower alkyl, aryl, hydroxy, lower alkoxy, $OCOBR_{10}$ where $R_{10}$ is alkyl, aryl, or heteroaryl and B is a direct bond or NH; or taken together are carbonyl or ethylenedioxy and the pharmaceutically acceptable salts thereof;

d.

A = 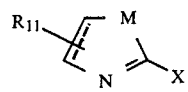

wherein ⸺ represents a double or single bond between two carbon atoms; $R_{11}$ is hydrogen or lower alkyl; M is NH, O, or S, and X is either a direct bond or NH; or

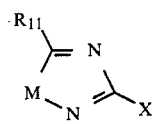

where X, M, and $R_{11}$ are the same as defined above, or e. $NHPR_{12}R_{13}$ wherein P is a bond or carbonyl; $R_{12}$ is lower alkyl, straight or branched; $R_{13}$ is $NR_{14}R_{15}$ wherein $R_{14}$ and $R_{15}$ are individually hydrogen, lower alkyl straight or branched or taken together to form a 5-, 6-, or 7-membered ring or a group as defined in 1a–1c; or $S(O)_n R_{16}$ where n is zero to two and $R_{16}$ is lower alkyl straight or branched, phenyl, and the pharmaceutically acceptable salts thereof.

DETAILED DESCRIPTION

The compound of formula I where $R_4$ is hydrogen may exist in tautomeric forms, for example, as illustrated by the following formulae.

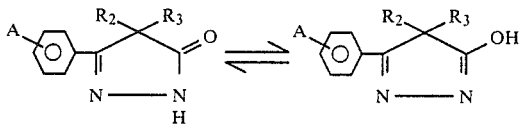

The present invention also relates to a compound of the formula

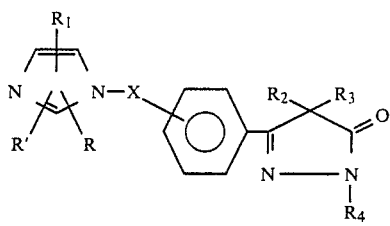

wherein R, $R_1$, R', X, $R_2$, $R_3$, and $R_4$ are defined above and pharmaceutically acceptable salts thereof.

Another aspect of the present invention is a compound of the formula

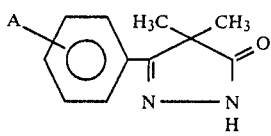

wherein A is as defined above and the pharmaceutically acceptable salts thereof. Preferable groups for A are imidazole or imidazole substituted by lower alkyl, S-lower alkyl, or $CH_2OH$; tetrahydrobenzimidazole, benzimidazole, or 1,2,4-triazole. Also preferred for A are 2-thiazoline, 4-hydroxypiperidine, 1,4-dioxa-8-azaspiro[4,5]decane, or N-methylpiperazine.

A particular aspect of the invention is 2,4-dihydro-5-[4-(1H-imidazol-1-yl)phenyl]-4,4-dimethyl-3H-pyrazol-3-one and a pharmaceutically acceptable salt thereof.

Another aspect of the present invention relates to a pharmaceutical composition for increasing cardiac contractility and/or for lowering blood pressure, said composition comprising an effective amount of a compound of formula I and a pharmaceutically acceptable carrier.

The present invention further relates to the method for increasing cardiac contractility and/or for lowering blood pressure in a patient requiring such treatment which comprises administering orally or parenterally in a solid or liquid dosage form to such patient an effective amount of a compound of the formula I and a pharmaceutically acceptable salt thereof in admixture with a pharmaceutically acceptable carrier.

The process for producing the pyrazol-3-ones of the formula I comprises reacting an appropriately substituted α,α-disubstituted-β-oxobenzenepropionic acid ester of the formula

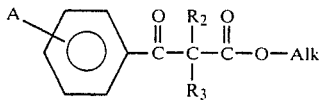

wherein A, $R_2$ and $R_3$ are as defined above and Alk is alkyl of from 1 to 4 carbon atoms, and preferably methyl or ethyl, with $R_4NHNH_2$, wherein $R_4$ is as defined above, at the boiling point of the solvent, which, for example, may be an alcohol such as methanol or ethanol.

The compounds of the formula I where Q is sulfur may be conveniently prepared from the above products where Q is oxygen by conventional means, such as treating the oxo compounds with phosphorus pentasulfide.

The starting acids may be prepared by alkylating in one step or in a step-wise manner depending on whether $R_2$ and $R_3$ are the same or different, the appropriately substituted alkyl ester of β-oxobenzenepropionic acid with an alkyl halide in the presence of sodium hydride in a polar aprotic solvent, such as dimethylformamide. The halide of preference is the iodide. The preferred ester is alkyl of from one to four 4 carbon atoms and especially methyl or ethyl.

The compounds of formula (I) are useful both in the free base form and in the form of acid addition salts. Both forms are within the scope of the invention. The acid addition salts are a more convenient form for use; and in practice, use of the salt form amounts to use of the base form. In practicing the invention, it was found convenient to form the sulfate, phosphate, or methanesulfonate salts. However, other appropriate pharmaceutically acceptable salts within the scope of the invention are those derived from mineral acids such as hydrochloric acid and sulfamic acid; and organic acids such as ethanesulfonic acid, benzenesulfonic acid, p-toluenesulfonic acid and the like, giving the hydrochloride, sulfamate, ethanesulfonate, benzenesulfonate, p-toluene-sulfonic, and the like respectively.

The acid addition salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The term "lower" in reference to alkyl and alkoxy means a straight or branched hydrocarbon chain of one to six carbon atoms such as, for example, methyl, ethyl, propyl, isopropyl, and the like. The term "halogen" includes fluorine, chlorine, bromine, and iodine but preferably is fluorine or chlorine.

The following examples will further illustrate the invention without, however, limiting thereto.

EXAMPLE 1

1-(Substituted phenyl)ethanones

A mixture of 0.2 moles of 4-fluoroacetophenone, 0.2 moles of an amine, 0.41 moles of potassium carbonate, 0.025 moles of cupric oxide and 80 ml of pyridine is refluxed under a nitrogen atmosphere for 24 to 48 hours. The pyridine is removed in vacuo and the residue is treated with chloroform and water. The chloroform layer is passed through silica gel and the solvent is removed. The residue is crystallized from methylene chloride-isopropyl ether.

According to the above method, the following compounds were obtained:

1-[4-(1H-Benzimidazol-1-yl)phenyl]ethanone as a crystalline solid, mp 134°–135° C.

1-[4-(4,5,6,7-Tetrahydro-1H-benzimidazol-1-yl)phenyl]ethanone as a crystalline solid, mp 94°–98° C.

1-[4-(1,4-Dioxa-8-azaspiro[4,5]dec-8-yl)phenyl]ethanone as a crystalline solid, mp 120°–121° C.

EXAMPLE 2

Substituted-β-oxobenzenepropanoic acid methyl esters

To a mixture of 0.1 mole of sodium hydride (60% suspension in Nujol), 12 ml of dimethyl carbonate and 15 ml of tetrahydrofuran is added dropwise a solution of a 0.05 moles of a 1-(substituted phenyl) ethanone in dimethylformamide-tetrahydrofuran. The mixture is heated at reflux for three hours. The reaction mixture is poured into water, the pH is adjusted to 9, and the mixture is extracted with methylene chloride. The solvent is removed and the residue crystallized from methylene chloride-isopropyl ether.

By the above method, the following compounds were obtained:

4-(1H-Benzimidazol-1-yl)-β-oxobenzenepropionic acid methyl ester as a crystalline solid, mp 130°–133° C.

4-(4,5,6,7-Tetrahydro-1H-benzimidazol-1-yl)-β-oxobenzenepropanoic acid methyl ester as a crystalline solid, mp 131°–133° C.

4-(1,4-Dioxa-8-azaspiro[4,5]dec-8-yl)-β-oxobenzenepropanoic acid methyl ester as a crystalline solid, mp 85°–88° C.

4-(1H-1,2,4-Triazol-1-yl)-β-oxobenzenepropanoic acid methyl ester as a crystalline solid, mp 123°–125° C.

EXAMPLE 3

Substituted-α,α-dimethyl-β-oxobenzenepropanoic acid methyl esters

To a slurry of 0.2 moles of sodium hydride (60% dispersion in Nujol) in 30 ml of dimethylformamide is added a solution of 0.1 moles of a substituted-β-oxobenzenepropanoic acid methyl ester in 100 ml of dimethylformamide at 15°–20° C. After the addition is completed, a solution of 0.1 moles of methyl iodide is added and stirring is continued for 20 hours at room temperature. The reaction mixture is poured into 1.2 l of water and is extracted with ether. The ether is removed and the residue triturated with petroleum ether.

Accordingly, the following compounds were obtained:

4-(1H-imidazol-1-yl)-α,α-dimethyl-β-oxobenzenepropanoic acid methyl ester as a crystalline solid, mp 91°–92° C. after recrystallization from isopropyl ether.

4-(1H-Benzimidazol-1-yl)-α,α-dimethyl-β-oxobenzenepropanoic acid methyl ester as an oil.

4-(4,5,6,7-Tetrahydro-1H-benzimidazol-1-yl)-α,α-dimethyl-β-oxobenzenepropanoic acid methyl ester as an oil.

4-(1,4-Dioxa-8-azaspiro[4,5]dec-8-yl)-α,α-dimethyl-β-oxobenzenepropanoic acid methyl ester as an oil.

4-(1H-1,2,4-Triazol-1-yl)-α,α-dimethyl-β-oxobenzenepropanoic acid methyl ester as an oil.

EXAMPLE 4

α-Ethyl-4-(1H-imidazol-1-yl)-α-methyl-β-oxobenzenepropanoic acid methyl ester

To a slurry of 2.49 g of sodium hydride (60% dispersion in Nujol) in 50 ml of dimethylformamide is added a solution of 24.4 g of 4-(1H-imidazol-1-yl)-β-oxobenzenepropanoic acid methyl ester in 75 ml of dimethylformamide at 15°–20° C. After the addition is completed 15.6 g of ethyl iodide is added and stirring is continued for 48 hours. The reaction mixture is filtered, poured into water, and the mixture is extracted with ether. Removal of the solvent and trituration with isopropyl ether gives an oil. A solution of 2.72 g of the oil in 10 ml of dimethylformamide is added to a slurry of 0.24 g of sodium hydride (60% dispersion in Nujol) at 15°–20°. A solution of 1.42 g of methyl iodide in 5 ml of dimethylformamide is added and stirring is continued for 20 hours at room temperature. The reaction mixture is filtered, poured into water, and is extracted with ether. Removal of the solvent gives an oil. The hydrochloride may be obtained from ethanol-isopropyl ether as a crystalline solid, mp 164°–166° C.

EXAMPLE 5

2,4-Dihydro-5-[substituted phenyl]-4,4-dimethyl-3H-pyrazol-3-ones

A solution of 1.0 g of a substituted-α,α-dimethyl-β-oxobenzenepropanoic acid methyl ester and 0.5 g of hydrazine hydrate in 10 ml of ethanol is refluxed overnight. On cooling, a crystalline product is deposited.

Accordingly, the following compounds are obtained:

2,4-Dihydro-5-[4-(1H-imidazol-1-yl)phenyl]-4,4-dimethyl-3H-pyrazol-3-one as a crystalline solid, mp 170°–171° C.

2,4-Dihydro-5-[4-(1H-benzimidazol-1-yl)phenyl]-4,4-dimethyl-3H-pyridazol-3-one as a crystalline solid, mp 301°–304° C.

2,4-Dihydro-5-[4-(4,5,6,7-tetrahydro-1H-benzimidazol-1-yl)phenyl]-4,4-dimethyl-3H-pyrazol-3-one as a crystalline solid, mp 245°–246° C.

2,4-Dihydro-5-[4-(1,4-dioxa-8-azaspiro[4,5]dec-8-yl)phenyl]-4,4-dimethyl-3H-pyrazol-3-one as a crystalline solid, mp 163.5°–165.5° C.

2,4-Dihydro-5-[4-(1H-1,2,4-triazol-1-yl)phenyl]-4,4-dimethyl-3H-pyrazol-3-one as a crystalline solid, mp 158°–160° C.

EXAMPLE 6

4-Ethyl-2,4-dihydro-5-[4-(1H-imidazol-1-yl)phenyl]-4-methyl-3H-pyrazol-3-one

A solution of 3.8 g of α-ethyl-4-(1H-imidazol-1-yl)-α-methyl-β-oxobenzenepropanoic acid methyl ester, 2.0 g of hydrazine hydrate and 25 ml of ethanol was refluxed for 20 hours. The ethanol is removed and the residue is treated with ether and water. Filtration of the solid gives after recrystallization from ethyl acetate, 2.7 g of a crystalline solid, mp 86°–88° C.

The usefulness of the compounds of the present invention as cardiotonic agents is demonstrated by their effectiveness in standard pharmacological test procedures, for example, in causing a significant increase in the myocardial contractility in the pentobarbital-anesthetized dog with low or minimal changes in heart rate and a moderate reduction in blood pressure. This test procedure is described in the following paragraphs.

Test for In Vivo Myocardial Intropic Activity in Anesthetized Dog

This screen consists of determining the effects of increasing intravenous doses of compound on mycardial contractility (dP/dt max of left ventricular blood pressure), heart rate, and aortic blood pressure of the pentobarbital-anesthetized dog.

Methods

Adult mongrel dogs of either sex are anesthetized with pentobarbital, 35 mg/kg, IV, and are subsequently maintained under anesthesia with a continuous infusion of pentobarbital, 3.5 mg/kg/hour. The trachea is intubated but the animals are permitted to breathe spontaneously. A cannula is inserted into the femoral vein for administering test agents. A Millar catheter tip pressure transducer or a fluid filled catheter is inserted into the ascending aorta via the femoral artery for measuring aortic blood pressure. A Millar catheter tip pressure transducer is passed into the left ventricle via the left carotid artery for measuring left ventricular blood pressure. Needle electrodes are placed subcutaneously for recording a lead II electrocardiogram (ECG).

Left ventricular and aortic blood pressures are recorded on a strip chart recorder. Heart rate, using a biotachometer triggered from the R wave of the ECG, and the first derivative of left ventricular blood pressure (dP/dt), obtained with a differentiator amplifier coupled to the corresponding pressure amplifier, are also recorded. A period of at least 30 minutes is utilized to obtain control data prior to administration of test compound.

Depending on solubility, the compounds are dissolved in 0.9% saline solution or in dilute HCl or NaOH (0.1 or 1.0 N) and are diluted to volume with normal saline. Ethanol or dimethylacetamide can be used as solvents if adequate dilutions can be made. Appropriate vehicle controls are administered when needed.

Each dose of the test compound is administered in a volume of 0.1 ml/kg over a period of one minute.

When tested by the above-described Anesthetized Dog Procedure, the compounds of the present invention, for example, 2,4-dihydro-5-[4-(1H-imidazol-1-yl)phenyl]-4,4-dimethyl-3H-pyrazol-3-one, when administered intravenously at a rate of about 0.01 to 0.31 mg/kg/min cause dose related significant increases in cardiac contractility with only low or minimal changes in heart rate and moderate lowering of blood pressure. Accordingly, the compounds of the present invention are also useful as antihypertensive agents.

I claim:

1. A compound of the formula

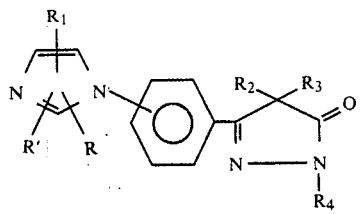

wherein $R_2$, $R_3$, and $R_4$ are independently hydrogen or alkyl of from one to six carbon atoms, $R_1$, $R'$, and $R$ are independently hydrogen, —$CH_2OH$, alkyl of from one to six carbon atoms, or alkoxy of from one to six carbon atoms, and the pharmaceutically acceptable salts thereof.

2. 2,4-dihydro-5-[4-(1H-imidazol-1-yl)phenyl]-4,4-dimethyl-3H-pyrazol-3-one or a pharmaceutically acceptable salt thereof.

3. 4-ethyl-2,4-dihydro-5-[4-(1H-imidazol-1-yl)phenyl]-4-methyl-3H-pyrazol-3-one or a pharmaceutically acceptable salt thereof.

* * * * *